United States Patent [19]
Friese et al.

[11] Patent Number: 5,739,441
[45] Date of Patent: Apr. 14, 1998

[54] SEAL SEAT FOR AN ELECTROCHEMICAL SENSOR ELEMENT

[75] Inventors: Karl-Hermann Friese, Leonberg; Helmut Weyl, Schwieberdingen; Romuald Fries, Weissach, all of Germany

[73] Assignee: Robert Bosch GmbH, Stuttgart, Germany

[21] Appl. No.: 727,677

[22] PCT Filed: Mar. 26, 1996

[86] PCT No.: PCT/DE96/00574

§ 371 Date: Oct. 17, 1996

§ 102(e) Date: Oct. 17, 1996

[87] PCT Pub. No.: WO96/35119

PCT Pub. Date: Nov. 7, 1996

[30] Foreign Application Priority Data

Apr. 29, 1995 [DE] Germany .......... 195 15 897.0

[51] Int. Cl.[6] ................ G01D 21/00; G01N 27/26
[52] U.S. Cl. ............... 73/866.5; 73/864.91; 204/424
[58] Field of Search ................ 73/866.5, 864.91; 204/428, 429, 424, 425, 426, 427

[56] References Cited

U.S. PATENT DOCUMENTS

| | | | |
|---|---|---|---|
| 4,240,890 | 12/1980 | Watanabe et al. | 204/428 X |
| 4,349,203 | 9/1982 | Schulke | 244/26 |
| 4,383,906 | 5/1983 | Sano et al. | 204/428 X |
| 4,572,009 | 2/1986 | Brauer et al. | 73/864.91 |
| 5,435,901 | 7/1995 | Friese et al. | 204/429 |

FOREIGN PATENT DOCUMENTS 4342731  2/1995  Germany.

*Primary Examiner*—Richard Chilcot
*Assistant Examiner*—Paul D. Amrozowicz
*Attorney, Agent, or Firm*—Spencer & Frank

[57] ABSTRACT

An arrangement of a sensor element of an electrochemical measuring sensor in a metallic housing is proposed, wherein the sensor element (13) in the form of a tube closed at one end rests with a metallic sealing ring (18) on a seal seat (16) implemented on the housing. The seal seat (16) is designed as a raised circular ring surface having a radius (r), with the sealing ring (18) orienting itself tangentially with respect to the radius (r).

6 Claims, 1 Drawing Sheet

SEAL SEAT FOR AN ELECTROCHEMICAL SENSOR ELEMENT

BACKGROUND OF THE INVENTION

The invention is based on an arrangement of a sensor wherein the sensor element, in the form of a tube closed at one end, rests with a metallic sealing ring on a seal seat formed on the housing element of an electrochemical measuring sensor in a metallic housing. The sensor elements of the electrochemical measuring sensors are configured, for example, in the so-called finger construction. The sensor element is a solid electrolyte body which is configured as a closed tube and fixed in a gas-tight manner in a metallic housing with a metallic sealing ring. In potential-free finger sensors, the metallic sealing ring must not contact the outer conductor track. For this purpose, the conductor track is coated with an electrically insulating layer upon which pressure is exerted by the sealing ring. A pressing of the edges of the sealing ring into the insulating layer would destroy the insulating layer and the potential-free feature would thus be eliminated. It is the object of the present invention to prevent this.

SUMMARY AND ADVANTAGES OF THE INVENTION

The problems according To the known arrangements are overcome according to the present invention by an arrangement of a sensor element of an electrochemical measuring sensor in a metallic housing, wherein the sensor element, in the form of a tube closed at one end, rests with a metallic sealing ring on a seal seat implemented on the housing, and the seal seat is designed as a raised circular ring surface having a radius (r).

The present invention as described above has the advantage that the sealing ring support line is disposed in the center of the seal seat cone on the sensor element and that a pronounced stress over the surface is present in the joining region between sealing ring and sensor element. This ensures increased production reliability, and the measuring sensor is improved with respect to its gas tightness and resistance to gasoline. The pronounced stress over the surface (wide contact pattern of the sealing ring) prevents possible crack formations in the insulating layer. This also prevents a diffusion of heavy metal ions into the insulating layer, thus maintaining the insulation resistance of the insulating layer even during thermally stressed continuous operation.

It is particularly advantageous to implement the radius for the support of the sealing ring with r=0.5–1.5 mm preferably r=1 mm. This creates a good seal seat which also does not entail any deformation of the sealing ring. Adjoining the radius, a free surface is configured for the sealing ring so that the sealing ring can orient itself tangentially relative to the line-shaped circular support formed by the radius. It is advantageous for the free surface to be cone-shaped.

BRIEF DESCRIPTION OF THE DRAWINGS

Two embodiments of the invention are illustrated in the drawing and explained In greater detail in the description below.

DETAILED DESCRIPTION OF THE PREFERRED EMBODIMENTS

Figure 1:
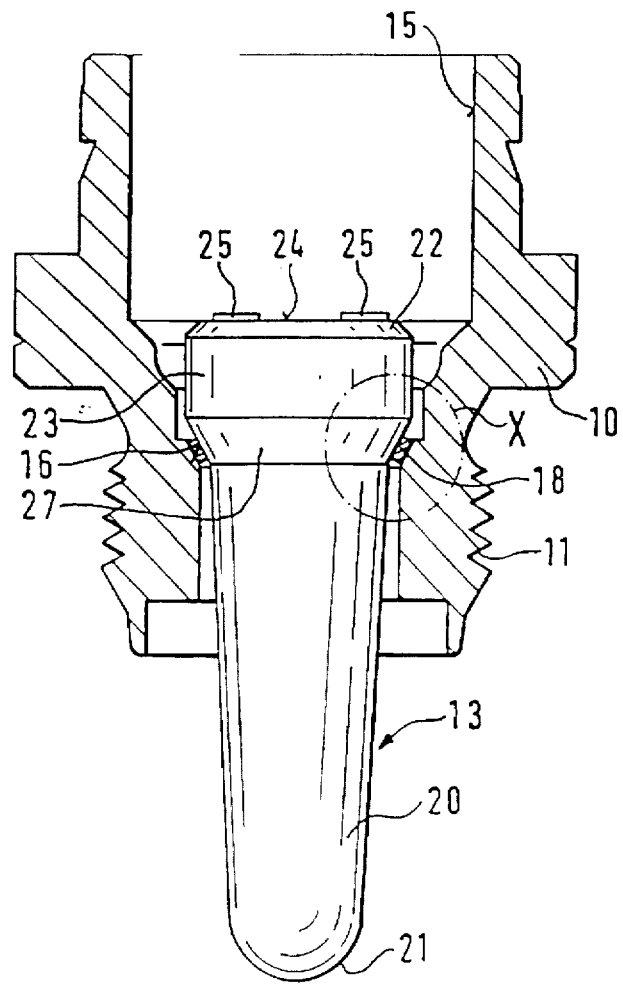
FIG. 1 shows a section through a detail of an electrochemical measuring sensor.

The electrochemical measuring sensor according to FIG. 1, shown in a detail, has a metallic housing 10 with a thread 11 as a fastening means or arrangements for the installation of the sensor in an exhaust gas pipe, not shown, and a sensor element 13. The housing 10 has a longitudinal bore 15 with a seal seat 16. The sensor element 13 with a metallic sealing ring 18 is seated on the seal seat 16.

The sensor element 13 is a tube-shaped solid electrolyte body 20 whose end section 21 is closed on the side of the gas to be measured. On the end section 22 on the side of the connection, the solid electrolyte body 20 is configured as a bulge-shaped head 23 with a ring-shaped front or end face 24.

On the outer side that is exposed to the gas to be measured, a measuring electrode, not shown in detail, is arranged on the solid electrolyte body 20. On the inside of the solid electrolyte body 20, a reference electrode is disposed, also not shown in detail, which is exposed to the reference gas, for example, air. Measuring electrode and reference electrode are respectively guided to electrode respective 25 arranged on the front face 24 by conductor tracks, also not shown.

On the bulge-shaped head 23, a sealing cone 27 is configured which is tapered toward the gas to be measured, by means of which cone the sensor element 20 rests on the sealing ring 18. The seal seat 16, the sealing ring 18 and the sealing cone 27 form a sealing zone X which is illustrated as an enlarged detail in FIGS. 2 and 3, respectively.

Figure 2:
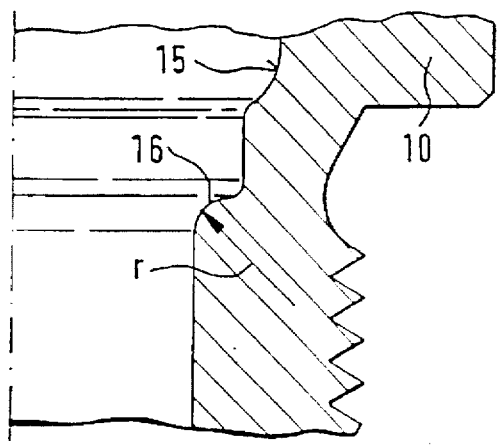
FIG. 2 shows an enlarged detail X with a first embodiment of a seal seat according to the invention.
Figure 3:
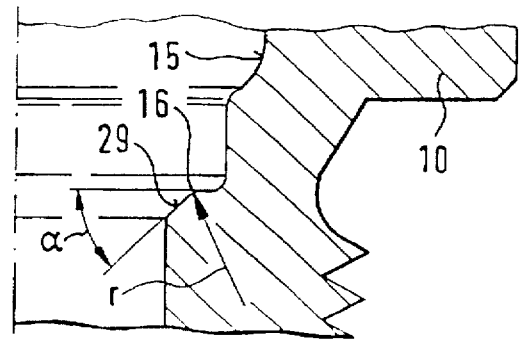
FIG. 3 shows the detail X with a second embodiment of a seal seat according to the invention.

In a first embodiment according to FIG. 2, the sealing seat 16 is provided with a radius r of, for example, 0.5–1.5 mm, preferably r =1 mm. Approximately in the center of the raised circular ring surface or seat 16 formed by the radius r, the sealing ring 18 rests also approximately with the center of its circular ring surface in a line-shaped manner. Thus, the sealing ring 18 can orient itself tangentially relative to the radius r so that the other surface of the sealing ring 18 adapts itself to the sealing cone 27. A pronounced stress over the surface is created in the joining region between sealing ring 18 and sealing cone 27. Thus, it is avoided that the sealing cone 27 resets only on one side on an edge of the sealing ring 18. The stress over the surface in the joining region between sealing ring 18 and sealing cone 27 thus ensures that the insulation layer for the electrode conductor track extending on the outer surface is not damaged or destroyed. A second embodiment for the design of the seal seat 16 ensues from FIG. 3. There, the support for the sealing ring is implemented with a radius r of, for example, r=0.6 mm. Toward the gas to be measured, the radius r is adjoined by a free surface 29 with a cone-shaped, tapering course of the longitudinal bore 15, with the cone having an angle α of, for example, 45°. The free surface 29 ensures that, here, the sealing ring 18 can also orient itself tangentially relative to the support formed by the radius r.

We claim:

1. An arrangement of a sensor element of an electrochemical measuring sensor in a metallic housing, wherein: the sensor element, in the form of tube closed at one end, has a conical sealing surface which rests with a metallic sealing ring on a seal seat implemented on the housing, the seal seat has a raised circular ring surface having a radius (r) of 0.5 to 1.5 mm, and the sealing ring adapts itself on the circular ring surface tangentially and automatically aligned with the conical sealing surface of the sensor element.

2. An arrangement according to claim 1, wherein the radius (r) is 1 mm.

3. An arrangement according to claim 1, wherein the sealing ring rests approximately with the center of its circular ring surface on the raised circular ring surface of the seal seat in a line-shaped manner.

4. An arrangement according to claim 3, wherein the sealing ring rests approximately in the center of the raised circular ring surface formed by the radius (r).

5. An arrangement according to claim 1, wherein in a direction toward the closed end of the sensor element, a free surface for the sealing ring adjoins the radius so that the sealing ring can orient itself tangentially relative to the radius (r).

6. An arrangement according to claim 5, wherein the free surface extends in a cone-shaped manner with an angle $\alpha$ of preferably 45° from the circular ring surface.

* * * * *